United States Patent [19]

Chu

[11] Patent Number: 4,987,224

[45] Date of Patent: Jan. 22, 1991

[54] METHOD OF PREPARATION OF 2',3'-DIDEOXYNUCLEOSIDES

[75] Inventor: Chung K. Chu, Athens, Ga.

[73] Assignee: University of Georgia Research Foundation, Inc., Athens, Ga.

[21] Appl. No.: 227,163

[22] Filed: Aug. 2, 1988

[51] Int. Cl.$^5$ .................. C07H 19/073; C07H 19/173

[52] U.S. Cl. ........................................ 536/23; 536/24; 536/124

[58] Field of Search ..................... 536/23, 24

[56] References Cited

U.S. PATENT DOCUMENTS

| | | | |
|---|---|---|---|
| 3,282,921 | 11/1966 | Verheyden et al. | 536/23 |
| 3,687,931 | 8/1972 | Verheyden et al. | 536/23 |
| 3,755,295 | 8/1973 | Verheyden et al. | 536/23 |
| 3,755,397 | 11/1973 | Etzold et al. | 556/409 |
| 3,817,982 | 6/1974 | Verheyden et al. | 536/23 |
| 4,071,680 | 1/1978 | Cook | 536/23 |
| 4,230,689 | 10/1980 | Bobek et al. | 424/74 |
| 4,526,988 | 7/1985 | Hertel et al. | 536/26 |
| 4,604,382 | 8/1986 | Lin et al. | 514/49 |

FOREIGN PATENT DOCUMENTS

| | | |
|---|---|---|
| 86301897.4 | 1/1986 | European Pat. Off. . |
| 86307071.0 | 8/1987 | European Pat. Off. . |
| 8603447 | 2/1985 | United Kingdom . |
| 8523878 | 9/1985 | United Kingdom . |

OTHER PUBLICATIONS

Anzai, et al., *Agr. Biol. Chem.* 37 (2), 345 (1973).
Baer, E., *Biochemical Preparations*, vol. 2, Editors E. G. Ball, John Wiley, New York, 1952, pp. 31–39.
Baker, Joseph and Schaub, *J. Am. Chem. Soc.* 5905 (1955).
Baker, Schaub and Williams, *J. Am. Chem. Soc.* 77, 7 (1955).
Broker, Modern Concepts and Therapeutic Challenges, *AIDS*, p. 303, Marcel Dekker, Inc., New York 1987.
Classon, et al., *Acta Chemica Scandinavica* B36, 251 (1982).
Colla, et al., *Eur. J. Med. Chem.-Chim. Ther.* 20(4), 295 (1985).
Chem. Abstract 101:192378c (1984).
Chem. Abstract 98:4753u (1983).
Chem. Abstract 96:69346s (1982).
Chem. Abstract 105:227205f (1986).
Dyatkina, N. B. *Soviet J. Biorg. Chem.* 12, 563 (1986).
Dyatkina and Azhayev, *Synthesis* 961 (Nov. 1984).
Fleet, Son and Drome, *Tetrahedron* 44 (2), 625 (1988).
Furman, et al., *Proc. Nat'l Acad. Sci., U.S.A.* 83, 8333 (1986).
Hafele and Jager, *Liebigs Ann. Chem.* 85 (1987).
Herdewijn, et al., *J. Med. Chem.* 30, 1270 (1987).
Horowitz, et al., *J. Org. Chem.* 29, 2076 (1984).
Horowitz, et al., *J. Am. Chem. Soc.* 86, 1896 (1964).
Horowitz, et al., *J. Org. Chem.* 31, 205 (1966).
Horowitz, et al., *J. Org. Chem.* 32, 817 (1967).
Horowitz, et al., *Tetrahedron Letters* 1343 (1966).
Jain, et al., *J. Org. Chem.* 39, 30 (1974).
Lin, et al., *J. Med. Chem.* 30, 440 (1987).
Lin, et al., *J. Med. Chem.* 21(1) 109 (1978).
Lin, et al., *J. Med. Chem.* 26, 1691 (1987).
Lin, T. S., et al., *J. Med. Chem.* 26, 544 (1983).
Krenitsky, et al., *J. Med. Chem.* 26(6) 891 (1983).
McCarthy, et al., *J. Am. Chem. Soc.* 88, 1549 (1966).
Mitsuya, et al., Nature, 325, 773 (1987).
Mitsuya, et al., *Proc. Natl. Acad. Sci. U.S.A.* 82, 7096 (1985).
Prisbe and Martin, *Synthetic Communications* 15 (5), 401 (1985).
Robins, et al., *Tetrahedron Letters* 25, 367 (1984).
Russell, et al., *J. Am. Chem. Soc.* 95 4025 (1973).
Tong, et al., *J. Org. Chem.* 30, 2854 (1965).
Webb, et al., *Nucleosides and Nucleotides* 7 (2), 147 (1988).
Yarcoan, et al., *New England Journal of Medicine*, 316, 557 (1987).
Lin, et al., *Biochemical Pharmocol.* 36 (17) 2713 (1987).
Chemical Abstracts 76:99976b (1972) Novak et al., Collect. Czech. Chem. Commun. 1971, 36(11) 3670–7.
Danilova et al. (1986) Tetrahedron Letters 27, 2489–2490.
Beer et al., (1982) Helv. Chim. Acta 65, 2570–2582.

*Primary Examiner*—Johnnie R. Brown
*Assistant Examiner*—Gary L. Kunz
*Attorney, Agent, or Firm*—Kilpatrick & Cody

[57] ABSTRACT

A general method of synthesis of 2',3'-dideoxynucleosides which is efficient, inexpensive and based on a readily available starting material, D-mannitol.

17 Claims, 3 Drawing Sheets

METHOD OF PREPARATION OF 2',3'-DIDEOXYNUCLEOSIDES

BACKGROUND OF THE INVENTION

The government has rights in this invention by virtue of grants from the Public Health Service and the National Institute of Allergy and Infectious Diseases.

This application is in the field of synthetic organic chemistry and specifically relates to an improved method of synthesis of 2',3'-dideoxynucleosides.

A nucleoside is a molecule consisting of a 5-carbon sugar and a purine or pyrimidine base. Addition of a phosphate group to the 5' position of the nucleoside converts it into a nucleotide. Nucleotides are the building blocks for the nucleic acids, RNA (ribonucleic acid) and DNA (deoxyribonucleic acid).

Several nucleosides have recently shown antiviral activity against human immunodeficiency virus type 1 and type 2 (HIV-1 and HIV-2, generally referred to herein as HIV). These two viruses are believed to cause AIDS, or acquired immunodeficiency syndrome.

AIDS is characterized by an imbalance in two basic types of immune system cells, helper/inducer T lymphocytes and suppressor T lymphocytes, with the ratio of suppressor cells to helper/inducer cells greatly elevated. Helper/inducer T cells, defined by a surface antigen called CD4, are responsible for the induction of most of the functions of the human immune system, including the humoral immune response involving the production of antibodies by B lymphocytes and the cell-mediated response involving stimulation of cytotoxic T cells. A condition associated with HIV is AIDS-related complex, or ARC. Most patients suffering from ARC eventually develop AIDS.

AIDS patients who succumb to opportunistic infections, and approximately half of all patients with Kaposi's sarcoma, die within two years of diagnosis. Attempts at reviving the immune systems in patients with AIDS have been unsuccessful.

Among the nucleosides shown to have antiviral activity, including anti-HIV activity, are 3'-azido-3'-deoxythymidine (AZT), 2',3'-dideoxycytidine (DDC), 2',3'-dideooxyadenosine (DDA), 2',3'-dideoxyinosine (DDI), 3'-azido-2',3'-dideoxyuridine (CS-87), 2',3'-dideoxy-2',3'-didehydrocytidine (D4C), 3'-deoxy-2',3'-didehydrothymidine (D4T) and 3'-azido-5-ethyl-2',3'-dideoxyuridine (CS-85).

3'-Azido-3'-deoxythymidine (AZT) has been found to be both an unusually potent antiviral agent against HIV-1 in vitro, as reported by H. Mitsuya, et al. *Nature*, 325, 773, (1987); R. Yarchoan, et al. *New Engl. J. Med.*, 316, 557, (1987); H. Mitsuya, et al. "Modern Concepts and Therapeutic Challenges" *AIDS*, p. 303 (Marcel Dekker, New York, 1987); H. Mitsuya, et al. *Proc. Nat'l Acad. Sci., USA,* 82 7096 (1985); and P. A. Furman, et al. *Proc. Nat'l. Acad. Sci., USA,* 83, 8333, (1986), and to decrease the mortality and opportunistic infections in patients with AIDS. Currently, AZT is the only chemotherapeutic agent available for AIDS patients. AZT was originally synthesized from thymidine as described by J. P. Horowitz, et al., in *J. Org. Chem.*, 29, 2076 (1984). It is currently produced from thymidine for pharmaceutical distribution. Unfortunately, supplies of AZT are now limited and expensive because of the high demand for thymidine, which is obtained from herring sperm.

Recently, a total synthesis of AZT by the condensation of thymine with a preformed 3'-azido-2'-deoxyribofuranose was reported by N. B. Dyatkina, et al., *Soviet J. Biorg. Chem.*, 12, 563 (1986); and G. W. J. Fleet, et al., *Tetrahedron,* 44, 625 (1988). However, in these methods, the intermediate azido sugar was prepared from D-xylose via the intermediate 1,2:3,5-di-O-isopropylidene-D-xylofuranose or methyl 3,5-O-isopropylidene-D-xylofuranose through a complex, multistep process.

3'-Azido-2',3'-dideoxyuridine (AZDU, CS-87) has also been found to be a potent antiviral agent against HIV-1 in vitro, as reported by R. F. Schinazi, et al., *J. Cell Biochem. Suppl.* 11D, 74, (1987); R. F. Schinazi, et al., *2nd International Conference on Antiviral Research,* Williamsburg, Va., April 100-14, 1988; *Antiviral Research,* 9, 84, (1988), and is presently undergoing preclinical toxicology studies. AZDU (CS-87) has been synthesized from 2'-deoxyuridine in an approach similar to the synthesis of AZT from thymidine developed by Horowitz, as described by T. S. Lin, et al. in *J. Med. Chem.,* 26, 544 (1983); C. K. Chu, et al., *J. Med. Chem.* in press. This synthetic route is likewise expensive due to the cost of the starting material for 2'-deoxyuridine.

There is a great need to develop a general synthetic scheme for 2',3'-dideoxynucleosides which is efficient, inexpensive, and based on a readily available starting material. It is essential that those suffering from AIDS be provided effective antiviral drugs at an affordable cost. In addition, an efficient, general synthetic route to these nucleosides will generate new derivatives for research.

It is therefore an object of the present invention to provide a general synthetic route to 2',3'-dideoxynucleosides.

It is a further object of the present invention to provide a synthetic route to 2',3'-dideoxynucleosides which is based on a readily available starting material.

It is a still further object of this invention to provide a synthetic route to 2',3'-dideoxynucleosides which is efficient and inexpensive.

It is another object of this invention to provide an efficient, inexpensive method of preparation of AZT and AZDU which is amenable to large scale production.

SUMMARY OF THE INVENTION

The present invention is a general method of synthesis of 2',3'-dideoxynucleosides which is efficient, inexpensive, and based on a readily available starting material, D-mannitol.

This method may be used to prepare antiviral substituted nucleosides on an industrial scale, alleviating the severe problem to date of supplying antiviral drugs at a low cost to those suffering from viral diseases. In particular, this method may be used to prepare AZT and AZDU, which are effective antiviral agents against HIV.

According to the present invention, D-mannitol is first converted into the acetal of D-glyceraldehyde. Through two alternative routes, the glyceraldehyde derivative is converted into the key intermediates, 1-O-(substituted)-3-(substituted)-2,3-dideoxy-5-0-(substituted)-D-(erythro or threo)-pentofuranoside, which may be reacted with a nitrogenous base such as a purine or pyrimidine to form a nucleoside.

The synthesis is a general route to a broad range of nucleosides, in that a wide variety of nucleophiles may be used to place substituents in the 3'-position of the nucleoside. Alternatively, the 3'-position may be unsubstituted. Furthermore, a wide variety of bases may be condensed with the pentofuranoside sugar.

DETAILED DESCRIPTION OF THE INVENTION

Figure 1:
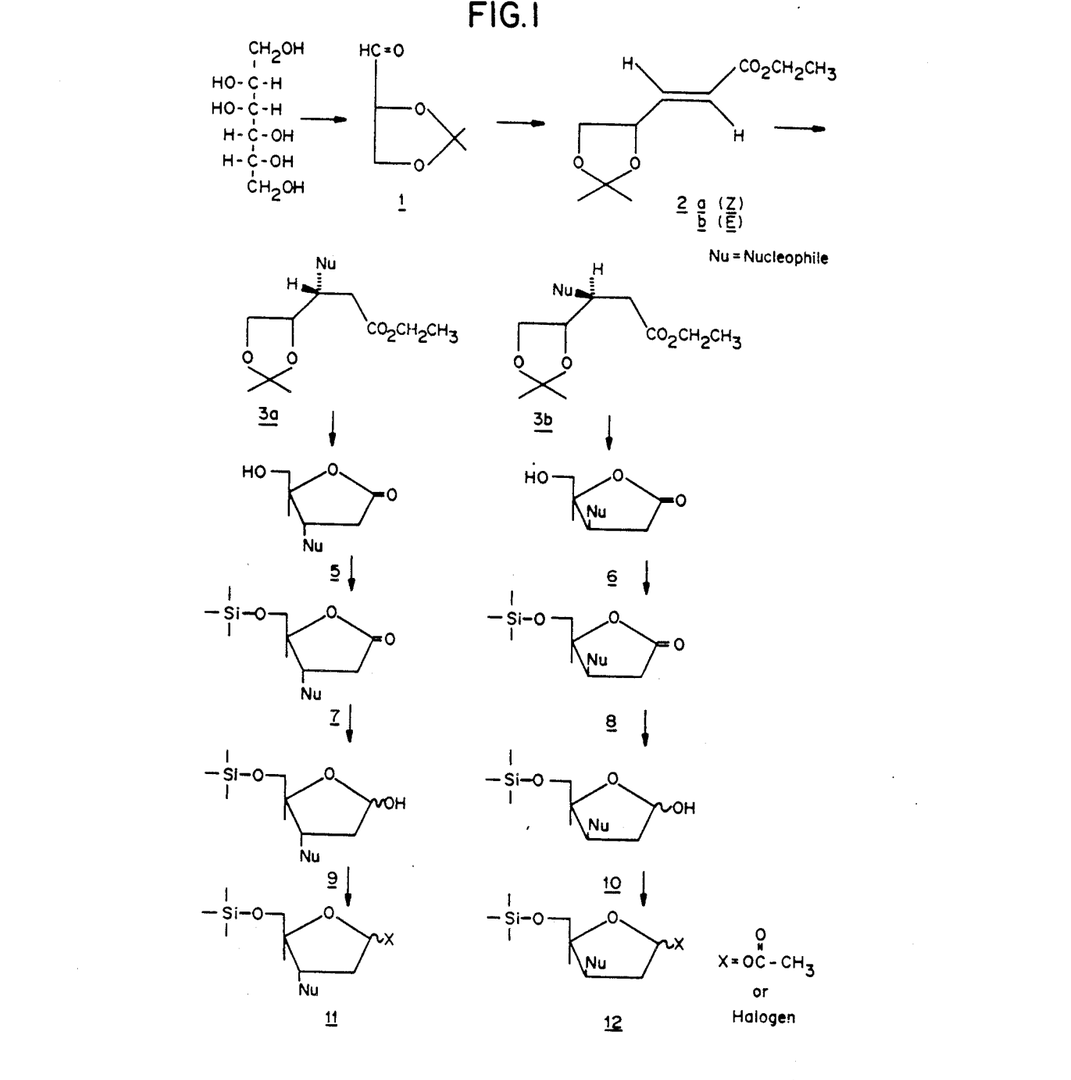
FIG. 1 is an illustration of Scheme I according to the present invention wherein D-mannitol is converted to 1-O-substituted-3-substituted-2,3-dideoxy-5-O-substituted-D-erythropentofuranoside.
Figure 2:
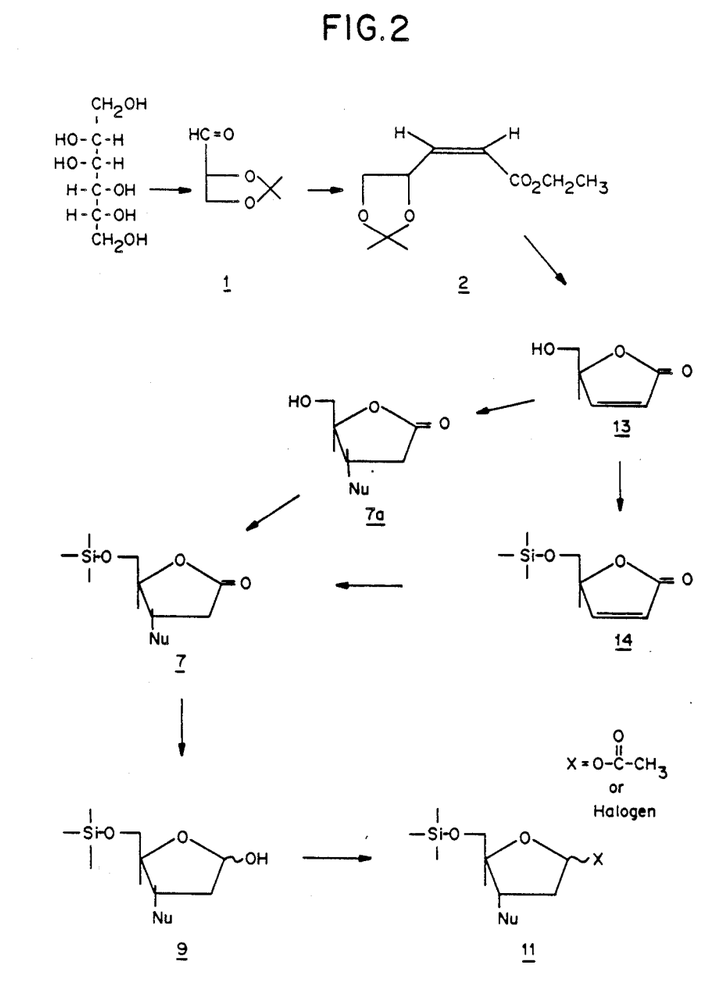
FIG. 2 is an illustration of Scheme II according to the present invention wherein D-mannitol is converted to 1-O-substituted-3-substituted- 2,3-dideoxy-5-O-substituted-D-(erythro or threo)-pentofuranoside.
Figure 3:
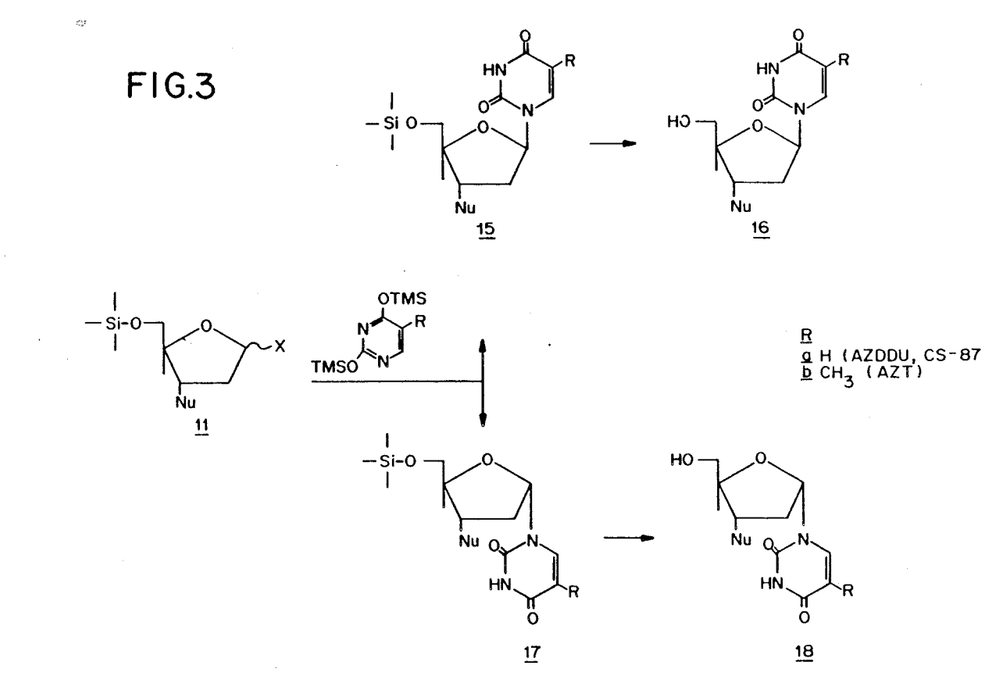
FIG. 3 is an illustration of Scheme III according to the present invention wherein 1-O-substituted-3-substituted-2,3-dideoxy-5-O-substituted-D-(erythro or threo)-pentofuranoside is converted to a 3'-substituted-2',3'-dideoxynucleoside.

The present invention is a general method of synthesis for 2',3'-dideoxynucleosides, which is efficient, inexpensive, and based on D-mannitol, a readily available six carbon polyhydroxy alcohol. The scheme provides two alternative routes, shown in FIGS. 1 and 2, to the formation of an 1-O-(substituted)-3-(substituted)-2,3-dideoxy-5-O-(substituted)-D-(erthyro or threo)pentofuranoside 11 or 12 which is reacted with a nitrogenous base such as purine or pyrimidine to form a nucleoside. Scheme I is illustrated in FIG. 1, and Scheme II in FIG. 2. The condensation of 11 with a purine or pyrimidine base to form a nucleoside is illustrated in FIG. 3.

In both Scheme I and Scheme II, D-mannitol is first converted into the acetal of D-glyceraldehyde in a 2-step process. E. Baer, *Biochemical Preparations*, Vol. 2, Editors E.G. Ball, John Wiley, New York, 1952, p. 31; B. Hafele and V. Jager, *Liebege Ann. Chem.* 85 (1987). In the first step, D-mannitol is reacted with p-toluenesulfonic acid in acetone to produce 1,2:5,6 diisopropylidene D-mannitol, which is reacted with lead tetraacetate in step two to form 1.

The next step in the reaction sequence, according to the present invention is a Wittig reaction carried out to convert the protected glyceraldyde into a mixture of $\alpha,\beta$-unsaturated esters, (Z)- and (E)- ethyl-(S)-(+)-3-(2,2-dimethyl-1,3-dioxalan-4-yl) acrylate, 2a and 2b. The E-isomer (E for german "entgegen", meaning opposite) is alternatively called a trans-alkene. The Z-isomer (Z for german "zusammen," meaning together) is alternatively called a cis-alkene. The choice of solvent has a large influence in a Wittig reaction over the ratio of Z to E isomers in the product mixture. In an aprotic solvent of low polarity such as acetonitrile ($CH_3CN$), benzene ($C_6H_6$) or chloroform ($HCCl_3$), as used in Scheme I, one obtains predominately the E-isomer, which is the thermodynamic product of reaction. In a polar solvent such as methanol ($CH_3OH$), as used in Scheme II, one gets predominately the Z-isomer, which is the kinetic product of reaction. The Z-isomer (cis alkene) has the correct configuration for internal cyclization to form the 2'-deoxyribose derivative of the nucleoside; the E-isomer (trans configuration) does not.

In Scheme I, according to the present invention, the mixture of predominately trans $\alpha,\beta$-unsaturated esters is then reacted with a nucleophile to form an enantomeric mixture of saturated esters, which is separated by chromatography and then cyclized and derivatized to form the key intermediates, 1-O-(substituted)-3-(substituted)-2,3-dideoxy-5-O-(substituted)-D-(erythro $\alpha$ or threo)-pentofuranosides 11 and 12.

In Scheme II, according to the present invention, the mixture of predominately cis $\alpha,\beta$-unsaturated esters is purified by chromatography, and the pure cis isomer 2a is cyclized and derivatized to form key intermediate 11.

Scheme I

In Scheme I, the mixture of (Z) and (E) $\alpha,\beta$-unsaturated esters, 2a and 2b with (Z) isomer 2a predominate, is reacted with a nucleophile in a Michael reaction to produce alkyl 3-(R)- and (S)-(substituted)-3-(2,2-dimethyl-1,3 dioxalan-4-yl)-propionate, 3a and 3b. The ratio between 3a and 3b will not be changed by the ratio of 2a/2b. For example, in the synthesis of AZT and CS-87, one may use lithium azide ($LiN_3$) or sodium azide ($NaN_3$) as the nucleophile. Alternatively, one may use flouride, bromide, iodide, chloride, cyanide, alkoxy, phenoxy, alkyl mercaptyl, thiophenyl, vinyl, acetylinic, thiocyano, phosphonomethylene, nitromethylene, cyanomethylene, and nitro. The alkyl regions of these nucleophiles may be substituted with hydrocarbons, halogens, nitro, thio groups or combinations of these. Thiophenol (or p-alkylthiophenol) may be used as a type of double bond protecting group, which can be taken off after the nucleoside is formed to regenerate the unsaturation at the 3', 4' position of the nucleoside. As with the other nucleophiles, thiophenol directs the glycosylation in such a way to give more $\beta$-isomer. Alternatively, the thiophenyl derivative can be reduced in the presence of a catalyst to form the 3'-unsubstituted nucleoside.

The Michael addition of lithium azide to the mixture of 2a and 2b may be done, for example, in a glacial acetic acid and water mixture at room temperature. If $CH_2NO_2$, $CH_2CN$ or $NO_2$ is the nucleophile, for example, a nonpolar solvent such as tetrahydrofuran, dioxane, benzene or toluene may be used as the solvent.

The R and S isomeric products of the Michael reaction, 3a and 3b, are then separated chromatographically. For example, vacuum flash chromatography with silica gel in a hexane: ethyl acetate solvent system will separate 3(R)- and (S)-azido-3-(2,2-dimethyl-1,3-dioxalan-4-yl)-propionate. The solvent and gel systems can be varied to separate the enantiomeric products of 2 with other nucleophiles.

Compounds 3a and 3b may then be separately cyclized to the corresponding 4(R)- and 4(S)-azido-3,4-dihydro-5(S)-(hydroxymethyl)-5(H)-furan-2-ones 5 and 6 by stirring 3a or 3b respectively in acid at a temperature range from $-50°$ C. to $100°$ C. for a period sufficient to complete the reaction.

In the present invention, the 5(S)-hydroxymethyl group of 5 or 6 is then protected by reacting 5 or 6 with a bulky reagent which reacts with alcohols and which is easily removed, to produce 4(R)- or 4(S)-(substituted)-3,4-dihydro-5(S)-(substituted)oxymethyl-5(H)-furan-2-one 7 and 8. Examples of alcohol protecting reagents include t-butylchlorodimethylsilane t-butylchlorodiphenylsilane, and triphenyl methanol. Other alcohol protecting groups known to those skilled in the art can be used.

The next step of Scheme I, according to the present invention, is the reduction of the carbonyl of lactone 7 or 8 to an alcohol to produce 3-substituted-5-O-(substituted)-2,3-dideoxy-$\alpha,\beta$-D-(erythro or threo)-pentofuranose 9 or 10, respectively. Suitable reducing agents include diisobutylaluminum hydride (DIBAL-H), lithium borohydride (LiBH$_4$), sodium bis(2-methoxyethoxy)aluminium hydride (Red-Al) or other sterically hindered reducing agents.

The final step of Scheme I is the protection of the 1-alcohol group of compound 9 or 10 with suitable alcohol protecting group or halogen (Cl or Br) to produce the key intermediates, 1-0-(substituted)-3-(substituted)-2,3-dideoxy-5-0-(substituted)-$\alpha,\beta$-D-(erythro or threo)-pentofuranoside, 11 and 12, respectively. One may prepare an acetate of the 1-alcohol group and then react it with a hydrogen halide to produce the corresponding halo derivative. For example, a suitable reagent is acetic anhydride.

The method of Scheme I will be better understood with reference to the following nonlimiting examples.

(Z)- and (E)-ethyl-(S)-(+)-3-(2,2-dimethyl-1,3-dioxalan-4-yl)acrylate 2a and 2b. A mixture of 1 (13.0 g, 100 mmol) and carbethoxymethylene-triphenylphosphorane (CMTP) (38.33 g, 110 mmol) in dry CH$_3$CN (200 mL) was refluxed for 2 h. Alternatively, one may use (CH$_3$CH$_2$)$_3$PCHCO$_2$CH$_2$CH$_3$. The mixture was then cooled, and after the removal of CH$_3$CN in vacuo the remaining residue was triturated with anhydrous diethyl ether (100 mL). The solid obtained was filtered off and the filtrate concentrated in vacuo to a small volume. Column chromatography of the filtrate with silica gel using hexanes-ethyl acetate (4:1) as the eluent yielded the (E/Z)-mixture (7:1) of 2, as a colorless liquid (12.5 g, 63%). The isomeric mixture can be separated by vacuum flash chromatography on a silica gel column (12×7 cm) using hexanes-ethyl acetate (8:1) as the eluent. The Z-isomer (1.79 g, 9%) obtained was found to be identical in physical and spectral characteristics with the product 2a produced in Scheme II from the reaction of CMTP with 1 in CH$_3$OH.

The E-enoate was separated as a more polar fraction (10.71 g, 54%). IR (Neat) 1720 (C=O) and 1665 (C=C); $^1$H NMR (CDCl$_3$) 1.29 (t, J=7.03 Hz, 3 H, CH$_2$CH$_3$), 1.41 (s, 3 H, CH$_3$), 1.45 (s, 3 H, CH$_3$), 3.67 (dd, J=7.03, 8.13 Hz, 1 H, H-5a), 4.21 (m, 3 H, CH$_2$C$_3$ and H-5b), 4.67 (m, 1 H, H-4), 6.08 (dd, J=1.32, 15.6 Hz, 1 H, H-2 trans), 6.89 (dd, J=5.49, 15.6 Hz, 1 H, H-3 trans). Anal. Calcd. for C$_{10}$H$_{16}$O$_4$: C, 59.99; H, 8.06. Found: C, 59.96; H, 8.06.

Ethyl 3-(R)- and (S)-azido-3-(2,2-dimethyl-1,3-dioxalan-4-yl)propionate 3a and 3b. To a solution of a mixture of (E/Z) enoates (7:1) 2 (5 g, 25 mmol) in glacial acetic acid (20 mL) was added dropwise, a solution of LiN$_3$ (7.8 g, 160 mmol) in H$_2$O (20 mL). The reaction mixture was stirred at room temperature for 24 h. Additional LiN$_3$ (7.8 g, 160 mmol) in water (20 mL) was added after the addition of acetic acid (20 mL) and then stirring was continued for another 48 h. The reaction mixture was neutralized with NaHCO$_3$ (40 g) and extracted with diethyl ether (100 mL×3). Combined etherical extracts were dried with MgSO$_4$ and evaporated in vacuo to yield a yellowish oil (5.5 g). The two isomeric azido esters 3a and 3b were then separated by vacuum flash chromatography (silica gel, hexanes-ethyl acetate 20:1).

The less polar azido ester 3a was obtained as a yellowish liquid.

The more polar azido ester 3b was separated as a yellow oil; IR (Neat) 2120 (N$_3$) and 1735 (C=O); $^1$H NMR (CDCl$_3$) 1.29 (t, J=7.25 Hz, 3 H, CH$_2$CH$_3$), 1.36 (s, 3 H, CH$_3$), 1.48 (s, 3 H, CH$_3$), 2.57 (d, J=6.18 Hz, 2 H), 3.7–4.35 (complex abs, 6 - H) Anal.

4(R)-Azido-3,4-dihydro-5(S)-(hydroxymethyl)-5(H)-furan-2-one 5. To a solution of azido ester 3a (1.5 g, 6.2 mmol) in ethanol (15 mL) was added conc. HCl (1.5 mL) dropwise. The mixture was stirred at room temperature for 12 h. Solvent was removed by distillation under vacuo and the residue was co-evaporated several times with C$_6$H$_6$ (10 mL). The pale yellow residue was chromatographed on a silica gel column using hexanes-ethyl acetate (4:1) as the eluent to yield 4-azidofuranone 5a as a colorless liquid (0.513 g, 52.9%). IR (Neat) 3600-3200 (broad, OH) 2110 (N$_3$) and 178 cm$^{-1}$ (C=O); $^1$H NMR (CDCl$_3$) 2.43–3.23 (m, 2 H, H-3), 2.84 (t, J=6 Hz, 1 H, OH), 3.63–4.15 (m, 2 H, CH$_2$ at 5), 4.35–4.55 (m, 2 H, H-4 and H-5). $^1$H NMR (CDCl$_3$+D$_2$O) 2.56 (dd, J=4.62, 18.02 Hz, 1 H, H-3a), 3.05 (dd, J=7.47, 18.02 Hz, 1 H, H-3b), 3.86 (qd, J=3.6, 12.74 Hz, 2H, CH$_2$ at 5), 4.3–4.55 (m, 2 H, H-4 and H-5 Anal. Calcd. for C$_5$H$_7$N$_3$O$_3$: C, 38.22; H, 4.49; N, 26.75. Found: C, 38.23; H, 4.53; N, 26.75.

4(S)-Azido-3,4-dihydro-5(S)-(hydroxymethyl)-5(H)-furan-2-one 6. A solution of azido ester 3b (1.0 g, 4.1 mmol) in ethanol (10 mL) was stirred with conc. HCl (1 mL) at room temperature for 12 h. Evaporation of the solvents and co-evaporation with C$_6$H$_6$ (10 mL) yielded a syrupy residue. The syrup was purified by vacuum flash chromatography on a silica gel column using hexanes-ethyl acetate (4:1) as the eluent. Azidolactone 6 was obtained as a colorless oil (0.42 g, 66%). IR (Neat) 3420 (OH), 2110 (N$_3$) and 1780 cm$^{-1}$ (C=O); $^1$H NMR (CDCl$_3$). The above compound was used in the next reaction without further purification.

4(R)-Azido-5(S)-[[(tert-butyldimethylsilyl)oxy]methyl]-3,4-dihydro-5(H)-furan-2-one. 7. To a solution of azidolactone 5 (2.2 g, 14 mmol) in anhydrous dimethylformamide (DMF) (64 mL) was added imidazole (1.85 g, 27.32 mmol) and t-butyldimethylsilyl chloride (2.53 g, 16.78 mmol). The reaction mixture was stirred at room temperature for 1 h and then the solvent was removed by distillation under reduced pressure. The residue was dissolved in CHCl$_3$ (125 mL), washed with H$_2$O (25 mL), dried with MgSO$_4$ and concentrated in vacuo to yield a colorless oil. Vacuum flash chromatography of the oil with silica gel using hexanes-ethyl acetate (8:1) as the eluent yielded 7 as colorless crystals (3.24 g, 85%), mp 35°-36° C. IR (Neat) 2110 (N$_3$) and 1790 cm$^{-1}$ (C=O); $^1$H NMR (CDCl$_3$) 0.08 (s, 6 H, CH$_3$), 0.89 (s, 9 H, t-butyl), 2.38–3.11 (m, 2 H, H-3), 3.84 (m, 2 H, CH$_2$ at 5), 4.40 (m, 2 H, H-4 and H-5). Anal. Calcd. for C$_{11}$H$_{21}$N$_3$O$_3$Si: C, 48.68; H, 7.80; N, 15.49. Found: C, 48.58; H, 7.82; N, 15.45.

4-(S)-Azido-5(S)-[[(tert-butyldimethylsilyl)oxy]methyl]-3,4-dihydro-5(H)furan-2-one 8. To a solution of azidolactone 6 (0.5 g, 3.32 mmol) in dry DMF (5 mL) was added imidazole (0.34 g, 5 mmol) followed by t-butyldimethylsilyl chloride (0.6 g, 3.99 mmol). The mixture was stirred at room temperature for 1 h. Solvent was then removed in vacuo and the residue was dissolved in CHCl$_3$ (30 mL). The CHCl$_3$ layer was washed with water (5 mL), dried with MgSO$_4$, and concentrated to yield an oil. The oil was purified by silica gel column chromatography using hexane-ethyl acetate (10:1) as the eluent to yield 0.619 g (75%) of 8 as a colorless liquid. IR (Neat) 2110 (N$_3$) and 1790 cm$^{-1}$ (C=O); $^1$H NMR (CDCl$_3$) 0.11 (s, 6 H, CH$_3$), 0.91 (s, 9 H, t-butyl), 2.75 (d, 2 H, H-3), 3.95 (m, 2 H, CH$_2$ at 5), 4.45 (m, 2 H, H-4 and H-5). Anal. Calcd. for $C_{11}H_{21}N_3O_3Si$: C, 48.58; H, 7.80; N, 15.49. Found: C, 48.74; H, 7.84; N, 15.40.

3-Azido-5-0-(tert-butyldimethylsilyl)-2,3-dideoxy-D-erythropentofuranose. 9. To a well stirred solution of silylated azidolactone 7 (4.0 g, 14.74 mmol) in $CH_2Cl_2$ (65 mL) under nitrogen and chilled to −78° C. (dry ice/acetone) was added DIBAL-H (1 M in Hexanes, 22.0 mL, 22.0 mmol), dropwise using a syringe. The colorless solution was maintained at −78° C. for 2 h and then quenched with a solution of $CH_3OH$ (2.6 mL) in $CHCl_3$ (130 mL). The reaction mixture was allowed to reach the room temperature, and washed with a solution of sodium tartrate (1 M, 130 mL). The organic layer was dried with $MgSO_4$ and concentrated in vacuo to yield a colorless oil (3.712 g), which was further purified by vacuum flash chromatography with silica gel using hexanes-ethyl acetate (16:1) as the eluent. Evaporation of the appropriate fractions yielded 9 as a colorless oil (3.1 g, 77%). IR (Neat) 3600–3100 (OH), and 2110 cm$^{-1}$ ($N_3$); $^1$H NMR ($CDCl_3$) 0.07 and 0.13 (s×2, 6 H, $CH_3$), 0.89 and 0.93 (s×2, 9 H, t-butyl), 2.00–2.5 (m, 2 H, H-2), 2.99 (d, J=6.37 Hz, 1 H, OH exchangeable), 3.5–3.8 (m, 2 H, H-5), 4.0–4.3 (m, 2 H, H-3 and H-4), 5.4–5.6 (m, 1 H, H-1). Anal. Calcd. for $C_{11}H_{23}N_3O_3Si$: C, 48.32; H, 8.48; N, 15.37. Found: C, 48.39; H, 8.52; N, 15.28.

3-Azido-5-0-(tert-butyldimethylsilyl)-2,3-dideoxy-$\alpha,\beta$-D-threopentofuranoside 10. A solution of azidolactone 8 (0.549 g, 2 mmol) in dry $CH_2Cl_2$ was cooled to −78° C. A 1 M solution of DIBAL-H in hexanes (3 mL) was added dropwise with stirring, under nitrogen atmosphere. Stirring was continued for 1 h at −78° C. and a solution of $CH_3OH$ (0.4 mL) in $CHCl_3$ (18 mL) was added. After the mixture was allowed to warm to room temperature a 1 M solution of sodium tartrate (18 mL) was added and stirred for 0.5 h. The $CHCl_3$ layer was separated, dried with $MgSO_4$, and concentrated to a pale yellow oil. Purification by chromatography (silica gel, ethyl acetate-hexanes 1:5) yielded 0.42 g (76%) of lactol as a colorless liquid. IR (Neat).

1-0-Acetyl-3-azido-2,3-dideoxy-5-0-(tert-butyldimethylsilyl)-D-erythro-pentofuranoside 11. Acetic anhydride (6.2 mL) was added to the azidolactol 9 (3.1 g, 11.34 mmol) followed by pyridine (5 drops) and the mixture was stirred at a room temperature for 15 h. Solvent was removed by evaporation under reduced pressure and the residue was purified by vacuum flash chromatography on a silica gel column using hexane-ethyl acetate (10:1) as the eluent. Evaporation of the appropriate fractions yielded an anomeric mixture (ratio 2:1) of 11 as a colorless oil (3.1 g, 87%). IR (Neat) 2110 ($N_3$) and 1755 cm$^{-1}$ (C=O); $^1$H NMR ($CDCl_3$) 0.06 and 0.09 (s×2, 6 H, $CH_3$), 0.89 and 0.92 (s×2, 9 H, t-butyl), 2.03 and 2.08 (s×2, 3 H, $COCH_3$), 2.15–2.5 (m, 2 H, H-2), 3.5–4.0 (m, 2 H, H-5), 4.0–4.35 (m, 2 H, H-3 and H-4), 6.30 (m, H-1). Anal. Calcd. for $C_{13}H_{25}N_3O_4Si$: C, 49.52; H, 7.93; N, 13.33. Found: C, 49.60; H, 8.03; N, 13.30.

1-0-Acetyl-3-azido-2,3-dideoxy-5-0-(tert-butyldimethylsilyl-$\alpha$, $\beta$-D-Threo-pentofuranoside 12. Azidolactol 10 (1.0 g, 3.66 mmol) was treated with acetic anhydride (2 mL) and pyridine (2 drops). The mixture was stirred at room temperature for 15 h. After removal of solvent in vacuo, the syrup obtained was filtered through a silica gel column using hexanes-ethyl acetate (16:1) as the eluent. Compound 12 was obtained as a colorless syrup (0.6 g, 52%). IR (Neat) 2110 ($N_3$) and 1750 cm$^{-1}$ (C=O); $^1$H NMR ($CDCl_3$)

Scheme II

In Scheme II, the acetal of D-glyceraldehyde 1 is reacted with carbethoxymethylene triphenylphosphorane or $(CH_3CH_2)_3PCHCO_2CH_2CH_3$ in a polar solvent to produce predominately the Z-isomer of 2, 2a (Z/E 8:1). The solvent may be anhydrous methanol, or other alcohols. The Z isomer 2a is less polar than the E isomer, and may be purified by vacuum flash or other suitable chromatography.

In the next step of Scheme II, according to the present invention, (Z)-alkyl-(S)-(+)-3-(2,2-dimethyl-1,3-dioxalan-4-yl) acrylate 2a is converted to an $\alpha,\beta$-unsaturated lactone, (S)-5-hydroxymethyl-5(H)-furan-2-one 13. This reaction may be performed under acidic conditions in anhydrous ethanol, using for example dilute HCl or p-toluenesulfonic acid.

Cyclization in anhydrous ethanol with dilute acid provides a yield of 90%. This procedure is a modification of the method of Hafele and Jager, *Liebigs. Ann. Chem.* 85 (1987), and is amenable to large scale synthesis (>100 grams).

The $\alpha,\beta$-unsaturated lactone 13 is then reacted with a nucleophile in a Michael addition to produce a 4-substituted-5-(S)-(hydroxymethyl)-3,4-dihydro-5(H)-furan-2-one 7. The nucleophile can attack the double bond from either the top of the lactone plane, producing a $\beta$-isomer, or it can attack the double bond from the bottom of the lactone plane, producing an $\alpha$-isomer. The $\alpha$-isomer is required in the synthesis of antiviral compounds such as AZT and CS-87. Compound 13 reacted with a Michael nucleophile yields a 6:1 mixture of $\alpha$ to $\beta$ isomers. Using the method of the present invention, however, the $\beta$ isomer may be entirely eliminated as a reaction product by introducing a bulky group such as t-butyl dimethylsilyl, t-butyl diphenylsilyl, or trityl at the 5-position of 13, before the Michael addition.

As in Scheme I, any suitable nucleophile may be used in the Michael addition. Examples are azide, flouride, bromide, iodide, chloride, cyanide, alkoxy, phenoxy, alkyl mercaptyl, thiophenyl vinyl, acetylinic, thiocyano, phosphonomethylene, nitromethylene, cyanomethylene, and nitro. The alkyl regions of these nucleophiles may be substituted with hydrocarbons, halogens, nitro, or thio groups or combinations of these.

In the next step of Scheme II, according to the present invention, the carbonyl of compound 7 is reduced to an alcohol to form 3-substituted-5-0-(substituted)-2,3-dideoxy-($\alpha,\beta$)-D-erythropentofuranose 9. Examples of suitable reducing agents include DiBal, $LiBH_4$, Red Al, and any other sterically hindered reducing agent. It has been found that 9 is an enantiomeric mixture of $\alpha$ and $\beta$ alcohols, however, this mixture has no effect on the stereochemistry of the final product. Again, the reduction of the lactone 7 to the lactol 9 proceeds in good yield (70–80%), contributing to the efficiency of the overall reaction.

In the final step of Scheme II, the key sugar intermediate in the formation of the nucleoside, 1-0-substituted-3-substituted-2,3-dideoxy-5-0-(substituted-($\alpha,\beta$)-D-erythropentofuranoside 11 is prepared by acetylation of 9. Acetic anhydride, acetic acid or any reagent that will provide an acetyl group is suitable as the reagent. Alternatively, the alcohol in 9 may be converted to chloride or bromide as an intermediate for glycosylation.

Scheme II will be better understood by reference to the following nonlimiting examples. (Z)- and (E)- ethyl (S)-(+)-3-(2,2-dimethyl-1,3-dioxalan-4-yl)acrylate 2a and 2b.

To an ice-cold solution of 2,3-0-isopropylidene-D-glyceraldehyde 1 (39.0 g, 300 mmol) in anhydrous $CH_3OH$ (1200 mL) was added carbethoxymethylene triphenylphophorane (314 g, 900 mmol). The mixture was removed by distillation under reduced pressure. Diethyl ether (1000 ml) was added to the residue, and the mixture was stirred with external cooling. The solid obtained was filtered off. The filtrate was concentrated in vacuo to a syrup, from which residual phosphine oxide was separated by filtration through a silica gel column using hexanes-ethyl acetate (4:1) as the eluent to give an (Z/E)-mixture (8:1) of the product. The Z- and E- isomers were separated by vacuum flash chromatography on silica gel column (19×8.5 cm) using hexane-ethyl acetate (8:1) as the eluent. The less polar Z-enoate 2a was obtained as a colorless liquid (32.0 g, 53%). IR (Neat) 1720 (C=O) and 1645 cm$^{-1}$ (C=C); $^1$H NMR (CDCl$_3$) 1.29 (t, J=7.03 Hz, 3 H, CH$_2$CH$_3$), 1.39 (s, 3 H, CH$_3$), 1.45 (s, 3 H, CH$_3$), 3.61 (dd, J=6.8, 8.13 Hz, 1 H, H-5), 4.25 (m, 3 H, CH$_2$CH$_3$ and H-5), 5.50 (dq, J=1.54, 6.59 Hz, 1 H, H-4), 5.83 (dd, J=1.54, 11.43 Hz, 1 H, H-2 cis), 6.38 (dd, J=6.89, 11.42 Hz, 1 H, H-3 cis). Anal. Calcd. for C$_{10}$H$_{16}$O$_4$: C, 59.99; H, 8.06. Found: C, 59.91; H, 8.08.

(S)-5-Hydroxymethyl-5(H)-furan-2-one 13. To a solution of (Z)-ethyl (S)-(+)-3-(2,2-dimethyl-1,3-dioxalan-4-yl)acrylate (35.0 g, 175 mmol) in anhydrous ethanol (300 mL) was added conc. HCl (23 mL). The reaction mixture was stirred at room temperature for 1 h. Solvent was removed by distillation in vacuo and the residue was co-evaporated with C$_6$H$_6$ (100 mL) several times. The resulting pale yellow syrup was then filtered through a silica gel column using CH$_2$Cl$_2$ diethylether (4:1) as the eluent. Evaporation of the appropriate fractions yielded a colorless syrup which on trituration with n-hexanes yielded a colorless solid. Recrystallization from diethyl ether yielded 4 (17.38 g, 87%), mp 38°–39° C. (lit mp 37°–39° C.); [α]$_D$= −145.3° (c 1, H$_2$O) [lit [α]$_D$= −145° (C 0.13 H$_2$O)]; IR (Neat) 3700–3150 (broad, OH), 1750 (C=O) and 1600 cm$^{-1}$ (C=C); $^1$H NMR (CDCl$_3$) 3.51–4.1 (complex abs, 3 H, CH$_2$ and OH), 5.16 (m, 1 H, H-5), 6.19 (dd, J=1.98, 5.71 Hz, 1 H, H-3), 7.53 (dd, J=1.54, 5.71 Hz, 1 H, H-4).

4(R)-Azido-3,4-dihydro-5(S)-(hydroxymethyl)-5(H)-furan-2-one 7a. To a solution of lactone 13 (4.56 g, 40 mmol) in glacial acetic acid (40 mL) was added a solution of LiN$_3$ (9.79 g, 200 mmol) in water (66 mL). The reaction mixture was stirred at room temperature for 72 h. The reaction mixture was periodically analyzed by TLC (hexanes-ethyl acetate 2:1) and additional amounts of acetic acid (20 mL) and LiN$_3$ (6.12 g, 125 mmol) in water (50 mL) were added. After 72 h of stirring, the reaction mixture was neutralized with NaHCO$_3$, and extracted with diethyl ether (100 mL×6). The combined etherical extracts were washed with a saturated solution of NaHCO$_3$ (25 mL×2) and water (50 mL×2), dried (MgSO$_4$) and concentrated to yield a pale yellow oil (3.4 g). $^1$H NMR of the product indicated the presence of α and β-azidolactones 5 and 6 in a 6:1 ratio. The isomeric mixture can be separated by vacuum flash chromatography in silica gel column using hexanes-ethyl acetate (2:1) as the eluent.

The less polar azidolactone 7 obtained as a colorless oil (2.89 g, 46%) was identical in physical and spectral characteristics with 5 obtained by the cyclization of 3a with HCL. IR (Neat) 3600–3100 (OH), 2110 (N$_3$) and 1780 cm$^{-1}$ (C=O).

The more polar β-azidolactone 6a obtained as a colorless oil (0.458 g, 7%) was found to be identical with the product obtained by the cyclization of 3b with HCl. IR (Neat) 3600–3100 (OH), 2100 (N$_3$) and 1780 cm$^{-1}$ (C=O).

4(R)-Azido-5(S)-[[(tert-butyldimethylsilyl)oxy]methyl]-3,4-dihydro-5(H)-furan-2-one. 7. To a solution of α-azidolactone 7a (which is the same as 5 from Scheme I) (2.2 g, 14 mmol) in anhydrous DMF (64 mL) was added imidazole (1.86 g, 27.32 mmol) and t-butyldimethylsilyl chloride (0.253 g, 16.78 mmol). The reaction mixture was stirred at room temperature for 1 h and solvent was removed by distillation under reduced pressure. The residue was taken in CHCl$_3$ (125 mL), was with H$_2$O (25 mL), dried (MgSO$_4$) and concentrated in vacuo to yield a colorless oil. Vacuum flash chromatography of the oil over a silica gel column using hexanes-ethyl acetate (8:1) as the eluent yielded 7 as colorless crystals (3.24 g, 85%), mp 35°–36° C. IR (Neat) 2110 (N$_3$) and 1790 cm$^{-1}$ (C=O); $^1$H NMR (CDCl$_3$) 0.08 (s, 6 H, CH$_3$), 0.89 (s, 9 H, t-butyl), 2.38–3.11 (m, 2 H, H-3), 3.84 (m, 2 H, CH$_2$ at 5), 4.40 (m, 2 H, H-4 and H-5). Anal. Calcd. for C$_{11}$H$_{21}$N$_3$O$_3$Si: C, 48.68; H, 7.80; N, 15.49. Found: C, 48.58; H, 7.82; N, 15.45.

5(S)-[[(tert-Butyldimethylsilyl)oxy]methyl]-5(H)-furan-2-one 14a. To a solution of the lactone 13 (2 g, 17.5 mmole) and imidozale (2.38 g, 34.5 mmole, 2.2 eq) in DMF (20 mL) was added t-butyldimethylsilyl chloride (2.9 g, 19.2 mm, 1.1 eq) and the reaction mixture allowed to stir for 1 h. The solvent was removed under reduced pressure and the residue was taken up into CHCl$_3$, washed with water, dried, filtered, and concentrated. The t-butyldimethylsilylether 14 was purified by silica vacuum flash column using 5% ethyl acetate-benzene as eluent to give 3.8 g (95%) of 14 as a thin oil which solidified a standing. IR (KBr) 2980–2910 ((CH$_3$)$_3$C—Si—O), 1770 cm$^{-1}$ (C=O). $^1$H NMR (CDCL$_3$) 0.063 (s, 6 H, 2×CH$_3$—Si), 0.875 (s, 9 H, t-butyl), 3.87 (t, J=5 Hz, 2 H), 5.15–4.9 (complex multiplet 1 H); 6.15 (dd, J=2, 6 Hz, 1 H), 7.49 (dd, J=2 Hz and 6 Hz, 1 H). Elemental analysis Calcd. for C$_{11}$H$_{20}$O$_3$Si: C, 57.89; H, 8.77. Found: C, 57.97; H, 8.86.

5(S)-[[(tert-butyldiphenylsilyl)oxy]methyl]-5(H)-furan-2-one 14b. To an ice-cold solution of lactone 4 (1.14 g, 10 mmole) and imidazole (1.33 g, 19.55 mmole) in dry DMF (30 mL) was added t-butyldiphenylsilyl chloride (3.28 g, 11.92 mmole). The mixture was stirred at 0°–5° C. for 0.5 h. The solvent was removed by distillation in vacuo. The residue was mixed with in CHCl$_3$ (50 mL), washed with water (10×2), dried (MgSO$_4$), and evaporated to yield a yellowish syrup. The syrup was purified by vacuum flash chromatography with silica gel using hexanes-ethyl acetate (8:1) as the eluent. Compound 14b was obtained as a crystalline solid (1.87 g, 53%) mp 86°–88° C. (lit, mp 79°–80° C.) IR (KBr) NMR (CDCl$_3$) 1.04 (s, 9 H, t-butyl), 3.89 (d, J=4.62 Hz, 2 H, CH$_2$), 5.5 (m, 1 H, H-5), 6.17 (dd, J=1.76, 5.71 Hz, 1 H, H-3), 7.3–7.7 (m 11 H, H-4 and 2×C$_6$H$_5$). Anal. Calcd. for C$_{21}$H$_{24}$O$_3$Si: C, 71.55; H, 6.86. Found: C, 71.42; H, 6.92.

4(R)-Azido-(5)-(S)-[[(tert-butyldiphenylsilyl)oxy]methyl]-3,4-dihydro-5(H)-furan-2-one 7 from 14. To a solution of lactone 14 (0.35 g, 1 mmole) in glacial acetic acid (3 mL) and THF (1 mL) was added a solution of LiN$_3$ (0.245 g, 5 mmol) in water (2 mL). The reaction mixture was stirred at room temperature for 72 hrs. The reaction mixture was analyzed by TLC (hexanes-ethyl acetate 2:1) at regular intervals (12 h). Additional acetic acid (0.3 ml) along with LiN$_3$ (0.123 g, 2.5 mmol) in H$_2$O (1 mL) was added. After the reaction was completed, water (5 mL) was added, and the solution neutralized with NaHCO$_3$ and extracted with ether (50×4). Combined etherial extracts were dried (MgSO$_4$) and concentrated to yield a colorless syrup (0.354 g). The syrup was purified by vacuum flash chromatography on silica gel column (6×3 cm) using hexanes-ethyl acetate (8:1) as the eluent. Less polar α-azidolactone 7 was isolated as colorless crystals after the evaporation of appropriate fractions (0.25 g). IR (KBr) $^1$H NMR (CDCl$_3$) 1.06 (s, 9 H, t-butyl), 2.54 (dd, J=3.3, 18.02 Hz, 1 H, H-2a), 3.01 (dd, J=7.25, 18.02 Hz, 1 H, H-2b), 3.83 (m, 2 H, H-5), 4.3–4.45 (m, 2 H, H-3 and H-4), 7.3–7.7 (m, 10 H 2×C$_6$H$_5$). Anal. Calcd. for C$_{21}$H$_{25}$O$_3$N$_3$Si: C, 63.77; H, 6.37; N, 10.62. Found: C, 63.60; H, 6.38; N, 10.53.

Later fractions of the eluent yielded unreacted starting material 20 (0.102 g).

Method B: To a solution of protected lactone 14 (0.228 g, 1 mmol) in a mixture of glacial acetic acid (1 mL) and THF (0.25 mL) was added a solution of LiN$_3$ (0.123 g, 2.5 mmol) in H$_2$O (1 mL) followed by 12-crown-4 (1 drop). The reaction mixture was stirred at room temperature for 72 h. Analyzed by TLC (hexane:ethyl acetate 4:1) was periodically performed. Additional LiN$_3$ (0.369 g) in water was added in order to complete the reaction. TLC indicated the formation of azidolactone 7 as the sole product of the reaction at the end of 36 hrs. However, as the reaction time increased, the formation of a new product with low Rf was observed. After neutralization with NaHCO$_3$, the reaction mixture was extracted with ether (15 mL×4). Etherial extracts were combined, dried (MgSO$_4$) and evaporated to yield a pale yellow syrup which was purified by vacuum flash chromatography (silica gel, ethyl acetate-hexanes 1.8). Azidolactone 7 was obtained as a colorless crystalline compounds identical with the product synthesized employing Method A, mp 35°–36° C.

3-Azido-5-0-(tert-butyldimethylsilyl)-2,3-dideoxy-α,β-D-erythro-pentofuranose. 9. To a well stirred solution of silylated azidolactone 7 (4.0 g, 14.74 mmol) in CH$_2$Cl$_2$ (65 mL) under nitrogen and chilled to −78° C. (dry ice/acetone) was added DIBAL-H (1 M in Hexanes, 22.0 mL, 22.0 mmol), dropwise using a syringe. The colorless solution was maintained at −78° C. for 2 h and then quenched with a solution of CH$_3$OH (2.6 mL) in CHCl$_3$ (130 mL). The reaction mixture was warmed to room temperature, and washed with a solution of sodium tartrate (1 M, 130 mL). The organic layer was dried (MgSO$_4$) and concentrated in vacuo to yield a colorless oil (3.712 g), which was further purified by vacuum flash chromatography on silica gel column using hexanes-ethyl acetate (16:1) as the eluent. Evaporation of the appropriate fractions yielded 9 as a colorless oil (3.1 g, 77%). IR (Neat) 3600–3100 (OH), and 2110 cm$^{-1}$ (N$_3$); $^1$H NMR (CDCl$_3$) 0.07 and 0.13 (s×2, 6 H, CH$_3$), 0.89 and 0.93 (s×2, 9 H, t-butyl), 2.00–2.5 (m, 2 H, H-2), 2.99 (d, J=6.37 Hz, 1 H, OH exchangeable), 3.5–3.8 (m, 2 H, H-5), 4.0–4.3 (m, 2 H, H-3 and H-4), 5.4–5.6 (m, 1 H, H-1). Anal. Calcd. for C$_{11}$H$_{23}$N$_3$O$_3$Si: C, 48.32; H, 8.48; N, 15.37. Found: C, 48.39; H, 8.52; N, 15.28.

1-0-Acetyl-3-azido-2,3-dideoxy-5-0-(tert-butyldimethylsilyl)-α,β-D-erythro-pentofuranoside 11. Acetic anhydride (6.2 mL) was added to the azidolactol 9 (3.1 g, 11.34 mmol) followed by pyridine (5 drops) and the mixture was stirred at a room temperature for 15 h. Solvent was removed by evaporation under reduced pressure and the residue was purified by vacuum flash chromatography on a silica gel column using hexane-ethyl acetate (10:1) as the eluent. Evaporation of the appropriate fractions yielded an anomeric mixture (ratio (2:1) of 11 as a colorless oil (3.1 g, 87%). IR (Neat) 2110 (N$_3$) and 1755 cm$^{-1}$ (C=O); $^1$H NMR (CDCl$_3$) 0.06 and 0.09 (s×2, 6 H, CH$_3$), 0.89 and 0.92 (s×2, 9 H, t-butyl), 2.03 and 2.08 (s×2, 3 H, COCH$_3$), 2.15–2.5 (m, 2 H, H-2), 3.5–4.0 (m, 2 H, H-5), 4.0–4.35 (m, 2 H, H-3 and H-4), 6.30 (m, m, H-1). Anal. Calcd. for C$_{13}$H$_{25}$N$_3$O$_4$Si: C, 49.52; H, 7.93; N, 13.33. Found: C, 49.60; H, 8.03; N, 13.30.

Condensation of the Sugar With Purine or Pyrimidine

Compound 11 is reacted with a nitrogenous base to form a nucleoside. Among the bases which may be used according to the present reaction are purines and pyrimidines. However, any compound containing a nitrogen which is capable of reaction with a center of election deficiency may be used. Purine bases include adenine N$^6$-alkyl purines, N$^6$-benzylpurine, and guanine. Pyrimidine bases include thymine, cytosine and uracil. If thymidine or cytidine derivatives are to be produced, the oxygens of thymine or the nitrogen of cytosine must be protected before condensation with the sugar, with, for example, a silyl group.

One of the advantages of the present invention is that compound 11 can be used as the intermediate in the synthesis of a wide variety of nucleosides, such as AZT, which has a thymine base, and CS-87, which has a uracil base.

Condensation of Compound 11 with the base may be carried out with, for example, anhydrous stannic chloride or trimethylsilyl triflate (trimethylsilyl trifluoromethanesulfonate).

For example, condensation of 11 with silylated thymine in 1,2-dichloroethane in the presence of trimethylsilyl triflate gave an α,β-mixture of 15b and 16b (66%), which could not be separated into individual isomers by column chromatography. However, the $^1$H NMR spectrum showed an α,β-mixture in a ratio of 1:1. The mixture was desilylated with n-tetrabutylammonium fluoride and then separated by silica gel column using a mixture of ethyl acetate-hexanes (10:1) as the eluent to give 17 and 18 (overall yield of 17 from 11 was 25%).

In the case of AZDU (CS-87), the condensation of 7 with silylated uracil in 1,2-dichloroethane with trimethylsilyl triflate followed by silica gel chromatography (chloroform methanol, 19:1) gave a 55% yield of α,β-mixture (33:67). After treatment of the inseparable α,β-mixture (33:67) with n-tetrabutylammonium fluoride and passage through a short silica gel flash column, AZDU (CS-87) was crystallized from isopropanol in the presence of its α-isomer 11a (overall yield of 10a from 7 was 20%).

Desilylation of 15 or 16 may be carried out with a variety of reagents, including acetic acid, trifluoroacetic acid, hydrogen flouride, n-tetrabutylammonium flouride, potassium flouride and pyridinium HCl. Acetic acid is preferred for commercial scale use because it is inexpensive. Other reagents for desilylation are known to those skilled in the art.

Condensation of the sugar with a purine or pyrimidine base according to the present invention will be better understood with reference to the following non-limiting examples.

2'-Azido-2',3'-dideoxy-5-0-(tert-butyldimethylsilyl)uridine 15a and 1-(3'-Azido-2',3'-dideoxy-5-0-(tert-butyldimethylsilyl)-D-erythro-pentofuranosyl)uracil 16a. Method A: Condensation using anhydrous stannic chloride in acetonitile. To a stirred solution of the anomeric acetates 11 (1 g, 3.17 mmol) and 2,4-bistrimethylsilyuracil (1.6 g, 6 mmol) in acetonitrile (50 mL, dried over 4A molecular sieves) was added anhydrous stannic chloride (1.65 g, 6.34 mmol) and the reaction mixture was allowed to stir at room temperature with protection from moisture for 18 h. At the end of this time, the reaction mixture was diluted with saturated sodium bicarbonate solution (25 mL) and extracted with ethyl acetate. The solvent layer was dried ($MgSO_4$), filtered and concentrated. The residue was chromatographed on a silica vacuum flash column using 30% ethylacetate-benzene as eluent to give a mixture of $\alpha$ and $\beta$ isomers which were solidified on the removal of solvent (0.95 g, 82%, ratio 67:33 by NMR). On trituration of this solid with diethylether the pure $\beta$-isomer 17a (9.509 g) was precipitated out: mp 133°–134° C.; $[\alpha]_D^{20} = -8.3°$ C. (C 0.55, $CH_3OH$) IR (KBr) 2120 cm$^{-1}$ ($N_3$). $^1H$ NMR ($CDCl_3$) 0.09 (s, 6 H, 2×$CH_3Si$), 0.912 (s, 9 H, 5-t-butylsi), 2.15 (dT, J=15, 2 Hz, 1 H, 2-H), 2.82 (dt, 1 H, J=15, 7 Hz, 1 H, 2-H), 3.7 (d, J=4 Hz, 2 H, H-5'), 4.2–4.4 (m, 2 H, H-3' and H-4'), 5.70 (dd, J=8, 2 Hz, 1 H, H-5'). 6.18 (dd, J=7, 2 Hz, 1 H, H-1'), 7.52 (d, J=8 Hz, 1 H, H-6), 8.42 (br, 1 H, NH, exchangeable). UV max (MeOH) 262 nm. Anal, Calcd. for $C_{15}H_{25}N_5O_4Si$: C, 49.04; H, 6.8; N, 19.07. Found: C, 49.10; H, 6.9; N, 19.06. Addition of hexanes to the mother liquor gave a solid which was found by $^1H$ NMR to be a mixture of 18 and 17 in a ratio of 30:70 (0.394 g).

Method B: Condensation using trimethylsilyl triflate in acetonitrile: A mixture of anomeric acetates 11 (0.14 g, 0.44 mmol) and 2,4-bis-trimethyl-silyloxy pyrimidine (0.35 g, 1.37 mmol) in dry acetonitrile (15 mL) was treated with trimethylsilyl triflate (0.149 g, 0.67 mmol) at room temperature for 24 hrs. Treatment of the reaction mixture as described under method A followed by the chromatographic purification (silica gel, $CHCL_3$—$CH_3OH$, 19:11) yields an $\alpha,\beta$ enantiomeric mixture (1:1) of 16a or 15a (0.125 g, 76%).

Method C: Condensation using trimethylsilyl triflate in $ClCH_2CH_2Cl$: Reaction of 11 (1.0 g, 3.17 mmol) with 2,4-bistrimethylsilyloxy pyrimidine (2.0 g, 7.8 mmol) in the presence of trimethylsilyl triflate (1.15 g, 5.2 mmol) in dry $ClCH_2CH_2Cl$ (20 mL) according to the procedure described under method B yielded an $\alpha:\beta$-mixture of 16a and 15a (0.65 g, 55%) in a ratio of 1:2, as indicated by $^1H$ NMR.

1-(3'-Azido-2',3'-dideoxy-D-erythro-pentofuranosyl)uracil 18a. To a stirred solution of 5'-t-butyldimethylsiloxy compound 16a (0.30 g, 0.817 mmol) in TMF (15 mL) was added a 1 M solution of tetrabutylammonium flouride in THF (1 mL, 1 mmol), after 0.5 h, the reaction mixture was concentrated and the residue chromatographed on a silica vacuum flash column using 5% $CH_3OH$—$CHCl_3$ as eluent. The fractions were combined and concentrated to give the $\alpha$-isomer as a hydroscopic foam. (0.165 g, 80%): $[\alpha]_D = -4.6°$ (C −0.49, $CH_3OH$. IR (KBr) 2120 cm$^{-1}$ ($N_3$); $^1H$ NMR (DMSO-$d_6$) 2.1 (dt, J=14, 4 Hz, 1 H, H-2'), 2.73 (dt, J=14.7 Hz, 1 H, H-2'), 3.47 (m, 2 H, H-5'), 4.1–4.45 (complex multiplet, 2 H, H-3' and 4'), 5.02 (t, J=5 Hz, 1 H, OH-5', exchangeable), 5.63 (d, J=8 Hz, 1 H, H-5), 6.07 (dd, J=7, 4 Hz, 1 H), 7.67 (d, J=8 Hz, 1 H, H-6), 11.27 (br, 1 H, NH, exchangeable). UV max 262 nm. Anal. Calcd. for $C_9H_{11}N_5O_4$: C, 42.68; H, 4.35; N, 27.66. Found:

3'-Azido-2',3'-dideoxyuridine (AZDU, CS-87) 17a. To a solution of the $\alpha,\beta$-mixture (30:70) of 5'-t-butyldimethylsilyl ethers 16a and 15a (0.26 g, 0.708 mmol) in THF (10 mL) was added a 1 M solution of tetrabutylammonium fluoride in THF (1 mL, 1.0 mmol) and the reaction mixture was allowed to stir. After 0.5 h, the reaction mixture was concentrated and the residue chromatographed on a silica vacuum flash column using 5% $CH_3OH$-ethyl acetate as eluent. The fractions containing the $\beta$-isomer (contaminated with some $\alpha$-isomer) were combined and concentrated. The residue was crystallized from isopropanol to yield 17a (0.066 g 53%): mp 168°–169° C. (lit mp 161°–163° C.; $[\alpha]_D = +79.25°$ (C 0.54, $CH_3OH$ (lit $[\alpha]_D=$$^1H$ NMR (DMSO-$d_6$) 2.33 (T, J=6 Hz, 2 H, H-2'), 3.6 (m, 2 H, H-5'), 3.85 (q, J=4 Hz, 1 H, H-4'), 4.4 (q, J=6 Hz, 1 H, H-3'), 5.18 (t, J=5 Hz, 1 H, H-1'), 7.83 (d, J=8 Hz, 1 H, H-6), 11.3 (br, 1 H, NH, exchangeable). IR (KBr) 2120 cm$^{-1}$ ($N_3$). UV max (MeOH) 261 mm. Anal. Calcd. for $C_9H_{11}N_5O_4$: C, 42.68; H, 4.35; N, 27.66. Found: C, 42.61; H, 4.41; N, 27.56. The deprotection of a $\beta$-mixture (1:2) of 16a and 15a from Method C (0.65 g) according to the above procedure yielded 0.167 g of AZDU (37%) (20% overall yield from 11).

3'-Azido-3'-deoxythymidine 13 and 1-(3'-Azido-2',3'-dideoxy- -D-erythro-pentofuranosyl)-thymine 15. Method A: Condensation with anhydrous stannic chloride in acetonitile. To a solution of the anomeric acetates 11 (1.0 g, 3.17 mmol) and 5-methyl-2,4-bis(trimethylsiloxy)-pyrimidine (4.2 g, 15.5 mmol) in dry $CH_3CN$ (125 mL) was added Tin (IV) chloride (0.55 mL, 4.7 mmol). The reaction mixture was stirred at room temperature for 18 h and filtered. The filtrate was neutralized with a 5% $NaHCO_3$ solution and extracted with ethyl acetate (50 mL×4). The ethyl acetate extract was dried ($MgSO_4$) and concentrated to yield a syrup (0.825 g, 68%). The syrup was dissolved in dry THF (20.9 mL). A 1 M solution of tetrabutylammonium fluoride (2.3 mL) was added dropwise and stirred at room temperature for 0.5 h. Solvent was removed by distillation in vacuo and the brownish syrup obtained was purified by column chromatography on silica gel (200–400 mesh, 45×3.2 cm) using ethyl acetate-hexanes (10:1) as the eluent to yield 15b and 16b in a combined yield of 78% (0.45 g).

3'-Azido-3'-deoxythymidine 17b was obtained as a less polar fraction (0.19 g, 31%), mp 120°–122° C. (lit. mp 118°–120° C.); $[\alpha]_D = +41.5°$ (C 1, $H_2O$) IR (KBr) 2100 ($N_3$) and 1750–1600 cm$^{-1}$; UV max ($CH_3OH$) 265.5 nm (lit. max ($CH_3OH$) 263 nm); $^1H$ NMR (($CH_3$)$_2SO$-$d_6$) 1.78 (d, J=0.88 Hz, 3H, $CH_3$-5), 2.32 (m, 2 H, H-2'), 3.61 (m, 2 H, H-5'), 3.8 (m, 1 H, H-3'), 4.39 (m, 1 H, H-4'), 5.18 (t, J=5.28 Hz, 1 H, OH, exchangeable), 6.09 (t, J=6.44 Hz, 1 H, H-1'), 7.67 (d, J=0.88 Hz, 1 H, H-6), 11.28 (broad, 1 H, NH, exchangeable).

More polar 1-(3'-azido-2',3'-dideoxy-D-erythro-pentofuranosyl) thymine 16b was obtained as colorless crystals (0.26 g, 45%) (hygroscopic). $[\alpha]_D = +42.6°$ C. (C 1, $H_2O$) [lit $[\alpha]_D^{20\ 20} = +41°$ (C 0.58, $H_2O$)]; IR (KBr) 2110 ($N_3$) and 1750–1600 cm$^{-1}$; UV max ($H_2O$) 268 nm; $^1H$ NMR ($CH_3\ _2SO$-$d_6$) 1.8 (d, J=1.2 Hz, 3 H, $CH_3$), 2.17 (m, 1 H, H-2a), 2.75 (1.2 Hz, 3H, $CH_3$), 2.17 (m, 1 H, H-2a), 2.75 (m, 1 H, H-2b), 3.49 (m, 2 H, H-5'), 4.28 (m, 2 H, H-3' and H-4'), 5.01 (t, J=5.56 Hz, 1 H, OH exchangeable), 5.99 (dd, J=4.39, 6.44 Hz, 1 H, H-1'), 7.54 (s, 1 H, H-6), 11.27 (broad, 1 H, NH, exchangeable). Method B: Condensation with trimethyltriflate in anhydrous $ClCH_2CH_2Cl$. Compound 11 (1.0 g, 3.17 mmol) was stirred with 5-methyl-2,4-bis(trimethylsiloxy)pyrimidine (2.1 g, 7.8 mmol) and trimethylsilyl triflate (1.15 g, 5.2 mmol) in anhydrous $ClCH_2CH_2Cl$ (20 mL), at room temperature, for 24 h. The product was recovered and purified by vacuum flash chromatography with silica gel using $CHCl_3:CH_3OH$ (19:1) as the eluent, yielding an α, β mixture of protected 15a and 16b (0.8 g, 66%) in 55:45 ratio as indicated by $^1H$ NMR spectrum.

This invention has been described with reference to its preferred embodiments. Variations and modifications of the method of preparing 2'3'-dideoxynucleosides will be obvious to those skilled in the art from the foregoing detailed description of the invention. It is intended that all of these variations and modifications be included within the scope of the appended claims.

I claim:

1. A process of preparing 2',3'-dideoxynucleosides, comprising:
   (a) preparing an acetal of glyceraldehyde from D-mannitol;
   (b) reacting the acetal of glyceraldehyde with a phosphorous ylid in a nonpolar solvent to produce a geometric isomeric mixture including E α,β-unsaturated esters;
   (c) reacting the geometric isomeric mixture with a nucleophile;
   (d) cyclizing a product of step (c) to a 4-substituted-3,4-dihydro-5-hydroxymethyl-5(H)-furan-2-one;
   (e) protecting the 5-hydroxymethyl group;
   (f) reducing the furan-2-one to a 3-substituted-5-0-substituted-2,3-dideoxy-D-erythro-pentofuranose;
   (g) activating the 1-0 position of the pentofuranose; and
   (h) reacting the activated pentofuranose with a nitrogenous base.

2. The process of claim 1 wherein the nitrogenous base is selected from the group consisting of purines and pyrimidines.

3. The process of claim 1, wherein the nucleophile is selected from the group consisting of azide, fluoride, bromide, chloride, iodide, cyanide, alkoxy, phenoxy, alkyl, alkyl mercaptyl, thiophenyl, p-alkylthiophenyl, vinyl, acetylinic, thiocyano, phosphonomethylene, nitromethylene, cyanomethylene and nitro, and wherein the alkyl regions of these nucleophiles may be substituted with hydrocarbons, halogens, nitro, or thio groups, or combinations of these.

4. The process of claim 1 further comprising selecting the protecting group for the 5-hydroxymethyl moiety from the group consisting of dimethylhexylsilyl, t-butyldimethylsilyl, t-butyldiphenylsilyl, and triphenylmethyl.

5. The process of claim 1, further comprising separating the isomers before cyclization.

6. The process of claim 3 wherein the nucleophile is thiophenyl or p-alkylthiophenyl.

7. The process of claim 6 further comprising removing the thiophenyl or p-alkylthiophenyl group after nucleoside preparation to regenerate unsaturation at the 3',4'-position of the nucleoside.

8. The process of claim 7 further comprising reducing the 3',4'-unsaturated nucleoside to a 3'-unsubstituted nucleoside.

9. A process of preparing a 2',3'-dideoxynucleoside, comprising:
   (a) preparing an acetal of glyceraldehyde from D-mannitol;
   (b) reacting the acetal of glyceraldehyde with a phosphorus ylid in a polar solvent to produce a geometric isomeric mixture including Z α,β-unsaturated esters;
   (c) cyclizing the Z α, β-unsaturated ester to a 5-hydroxymethyl-5(H)-furan-2-one;
   (d) reacting the furan-2-one with a nucleophile to produce a 4-substituted-5-hydroxymethyl-3,4-dihydro-furan-2-one;
   (e) protecting the 5-hydroxymethyl group;
   (f) reducing the furan-2-one to a 3-substituted-5-0-substituted-2,3-dideoxy-D-erythro-pentofuranose;
   (g) activating the 1-0 position of the pentofuranose; and
   (h) reacting the activated pentofuranose with a nitrogenous base.

10. The process of claim 9 comprising adding a sterically hindered substituent to the 5-hydroxymethyl position before reaction with the nucleophile.

11. The process of claim 9 wherein the nitrogenous base is selected from the group consisting of purine and pyrimidine bases.

12. The process of claim 10 wherein the sterically hindered substituent is selected from the group consisting of dimethylhexylsilyl, t-butyldiphenylsilyl, t-butyldimethylsilyl and triphenylmethyl.

13. The process of claim 9, further comprising separating the isomers before cyclization.

14. The process of claim 9, wherein the nucleophile is selected from the group consisting of azide, fluoride, bromide, chloride, iodide, cyanide, alkoxy, phenoxy, alkyl, alkyl mercaptyl, thiophenyl, p-alkylthiophenyl, vinyl, acetaylinic, thiocyano, phosphonomethylene, nitromethylene, cyanomethylene and nitro, wherein the alkyl regions of these nucleophiles may be substituted with hydrocarbons, halogens, nitro, or thio groups or combinations of these.

15. The process of claim 14 wherein the nucleophile is thiophenyl or p-alkylthiophenyl.

16. The process of claim 15 further comprising removing the thiophenyl group after nucleoside preparation to regenerate unsaturation at the 3',4'-position of the nucleoside.

17. The process of claim 16 further comprising reducing the 3',4'-unsaturated nucleoside to a 3'-unsubstituted nucleoside.

* * * * *